(12) United States Patent  
Serhan et al.

(10) Patent No.: US 7,741,368 B2
(45) Date of Patent: *Jun. 22, 2010

(54) APPROACH TO ANTIMICROBIAL HOST DEFENSE WITH MOLECULAR SHIELDS WITH EPA AND DHA ANALOGS

(75) Inventors: Charles N. Serhan, Needham, MA (US); Sean P. Colgan, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1165 days.

This patent is subject to a terminal disclaimer.

(21) Appl. No.: 11/353,436

(22) Filed: Feb. 14, 2006

(65) Prior Publication Data

US 2006/0128804 A1    Jun. 15, 2006

Related U.S. Application Data

(63) Continuation of application No. 10/323,867, filed on Dec. 18, 2002, now Pat. No. 7,030,159.

(60) Provisional application No. 60/342,138, filed on Dec. 18, 2001.

(51) Int. Cl.
  *A61K 31/20* (2006.01)
  *A61K 31/205* (2006.01)
  *A61K 31/22* (2006.01)
(52) U.S. Cl. .................. 514/560; 514/549; 514/552
(58) Field of Classification Search ................ 514/560, 514/549, 552
See application file for complete search history.

(56) References Cited

U.S. PATENT DOCUMENTS

| 4,201,211 | A | 5/1980 | Chandrasekaran et al. |
| 4,666,701 | A | 5/1987 | Horrobin et al. |
| 4,810,424 | A | 3/1989 | Gerwick et al. |
| 5,409,955 | A | 4/1995 | Bockow et al. |
| 5,411,988 | A | 5/1995 | Bockow et al. |
| 5,604,258 | A | 2/1997 | Ferrante et al. |
| 5,650,157 | A | 7/1997 | Bockow |
| 5,709,855 | A | 1/1998 | Bockow et al. |
| 5,752,238 | A | 5/1998 | Dedrick |
| 5,814,599 | A | 9/1998 | Mitragotri et al. |
| 5,846,974 | A | 12/1998 | Kallman et al. |

(Continued)

FOREIGN PATENT DOCUMENTS

GB    2033745 A1    5/1980

(Continued)

OTHER PUBLICATIONS

Testa "Prodrug research: futile or fertile?" Biochemical Pharmacology, 2004, vol. 68, pp. 2097-2106.*

(Continued)

*Primary Examiner*—Shengjun Wang
(74) *Attorney, Agent, or Firm*—Scott D. Rothenberger; Colin L. Fairman; Fulbright & Jaworski LLP

(57) ABSTRACT

Methods to cause tissue, such as mucosal cells, to express increased amounts of bactericidal permeability increasing protein (BPI) are described. Various BPI inducing agents include icosapentanoic acid (EPA) analogs and docosahexaenoic acid (DHA) analogs.

6 Claims, 5 Drawing Sheets

OKF-6

Caco2

2° only

U.S. PATENT DOCUMENTS

| | | | |
|---|---|---|---|
| 5,861,399 | A | 1/1999 | Seed et al. |
| 5,912,006 | A | 6/1999 | Bockow et al. |
| 6,030,715 | A | 2/2000 | Thompson et al. |
| 6,069,109 | A | 5/2000 | Kao et al. |
| 6,117,911 | A | 9/2000 | Grainger et al. |
| 6,201,022 | B1 | 3/2001 | Mease et al. |
| 6,232,467 | B1 | 5/2001 | Petasis et al. |
| 6,259,699 | B1 | 7/2001 | Opalka et al. |
| 6,272,474 | B1 | 8/2001 | Garcia |
| 6,336,105 | B1 | 1/2002 | Conklin et al. |
| 6,949,664 | B2 | 9/2005 | Petasis |
| 7,030,159 | B2 | 4/2006 | Serhan et al. |
| 7,053,230 | B2 | 5/2006 | Serhan et al. |
| 7,341,840 | B2 | 3/2008 | Serhan et al. |
| 2002/0055539 | A1 | 5/2002 | Bockow et al. |
| 2002/0111505 | A1 | 8/2002 | Serhan |
| 2003/0236423 | A1 | 12/2003 | Petasis |
| 2004/0044050 | A1 | 3/2004 | Goodman et al. |
| 2005/0228047 | A1 | 10/2005 | Petasis |
| 2006/0128804 | A1 | 6/2006 | Serhan et al. |
| 2006/0293288 | A1 | 12/2006 | Serhan et al. |
| 2008/0096961 | A1 | 4/2008 | Serhan et al. |

FOREIGN PATENT DOCUMENTS

| | | |
|---|---|---|
| JP | XP-002184773 | 7/1990 |
| JP | 5186342 | 7/1993 |
| WO | WO 91/16914 | 11/1991 |
| WO | WO 98/46588 | 10/1998 |
| WO | 9956727 A2 | 11/1999 |
| WO | 9956727 A3 | 11/1999 |
| WO | 0032210 A1 | 6/2000 |
| WO | WO 00/74632 | 12/2000 |

OTHER PUBLICATIONS

Slots, et al., "General Health Risk of Periodontal Disease", International Dental Journal, Dec. 2001, 51(6), pp. 417-422.

Green, Gary A., "Understanding NSAIDS: From Aspirin to COX-2", Clinical Cornerstone, Sports Medicine 2001, 3(5), pp. 50-59.

Merck Index, "Gingivitis", Copyright © 1995-2007 Merck & Co., Inc., Whitehouse Station, NJ, USA, Last Full Version, Feb. 2003, 3 pgs.

Stella, Valentino J., "Expert Opinion of Therapeutic Patents", Prodrugs as Therapeutics, 2004, 14(3), pp. 277-280.

Wolff et al., "Burger's Medicinal Chemistry and Drug Discovery", $5^{th}$ Ed., vol. 1, pp. 975-977, 1994.

Dragoli et al., "Parallel Synthesis of Prostaglandin $E_1$ Analogues", J. Comb. Chem., 1999, pp. 534-539.

J.W. Karanian et al., "Inhibitory Effects of n-6 and n-3 Hydroxy Fatty Acids on Thromboxane (U46619)-Induced Smooth Muscle Contraction", The Journal of Pharmcology and Experimental Therapeutics, vol. 270, No. 3, pp. 1105-1109, 1994, XP-009087752.

Khalfoun, B., "Docosahexaenoic and Eicosapentaenoic Acid Inhibit Human Lymphoproliferative Responses In Vitro but not the Expression of T cell Surface Activation Markers", Scand. J. of Immunol., vol. 43, pp. 248-256, 1996, XP-000878923.

Croset, M., et al., "Inhibition by Lipoxygenase Products of TXA2-Like Responses of Platelets and Vascular Smooth Muscle", Biochemical Pharmacology, vol. 37, No. 7, pp. 1275-1280, 1988, XP-002445509.

"Epolinsatures", Bulletin De La Societe Chimique de France, No. 3, pp. 419-432, 1989.

Khair-El-Din, et al. "Transcription of the Murine iNOS Gene is Inhibited by Docosahexaenoic Acid, a Major Constituent of Fetal and Neonatal Sera as Well as Fish Oils", J. Exp. Med., vol. 183, pp. 1241-1246, 1996.

Schmedtje, Jr. et al., "Hypoxia Induces Cyclooxygenase-2 via the NF- Kb p65 Transcription Factor in Human Vascular Endothelial Cells", J. Biol. Chem., vol. 272, No. 1, 1997, pp. 601-608.

Serhan et al., "Novel functional sets of lipid-derived mediators with Anti-inflammatory Actions generated from omega-3 fatty acids via cyclooxygenase 2-nonsteroidal anti-inflammatory drugs and transcellular processing", J. Exp. Med., vol., 192, No. 8, 2000, pp. 1197-1204.

Takeshi Terano et al., "Eicosapentaenoic acid and docosahexaenoic acid inhibit vascular smooth muscle cell proliferation by inhibiting phosphorylation of Cdk2-cyclinE complex", Biochem. Biophys. Res. Comm., vol. 254, pp. 502-506.

Chemical Abstracts online citation, AN:2004:143088, retrieved Aug. 15, 2007, from STN, Columbus, OH.

Hong, et al. "Rainbow trout (Oncorhynchus mykiss) brain cells biosynthesize novel docasahexaenoic acid-derived resolvins and protectins—mediator lipidomic analysis", Prostaglandins & Other Lipid Mediators, Elsevier, vol. 78, No. 1-4, Jun. 13, 2005, pp. 107-116. XP005174168.

Serhan, Charles N. et al. "Anti-Inflammatory Actions of Neuroprotectin D1/Protectin D1 and it's Natural Stereoisomers: Assignments of Dihydroxy-Containing Docosatrienes", Journal of Immunology, 176(3), 1848-1959 Coden: J01MA3; ISSN 0022-1767, Feb. 1, 2006. XP002429095.

Levy, Bruce D. et al. "Protectin D1 is Generated in Asthma and Dampens Airway Inflammation and Hyperresponsiveness," The Journal of Immunology, 2007, 178: 496-502.

PCT/US2006/038326 International Search Report dated Apr. 23, 2007.

PCT/US2006/000306 International Search Report dated Jul. 14, 2006.

PCT/US2003/25336 International Search Report dated Feb. 16, 2004.

PCT/US2001/05196 International Search Report dated Jul. 19, 2002.

EP 06 02 2386 European Search Report dated Oct. 5, 2007.

PCT/US2005/12552 International Search Report dated Aug. 24, 2005 (in name of Trustees of Boston University).

PCT/US2006/011222 International Search Report dated Oct. 5, 2007.

PCT/US2005/009056 International Search Report dated Nov. 16, 2005.

Knapp, Howard R., et al., "Bactericidal Effects of Polyunsaturated Fatty Acids", The Journal of Infectious Diseases, vol. 154, No. 1, 1986 pp. 84-94.

Cooper, S.F., et al., "Identification of Antibacterial Fatty Acids from Phaeodactylum tricomtum grown i dialysis culture", The Faculty Press, 1985, pp. 28-36.

Karanian, J.W. et al., "Physiological functions of hydroxy-docosahexaenoic acid", Abstract, XP-002200246, 1993.

Hill, E.M. et al., "Identification and egg hatching activity of monohydroxy fatty acid eicosanoids in the barnacle Balanus balanoides", Abstract, XP-002200247, 1992.

Ganz, T. et al., "Antimicrobial peptides of phagocytes and epithelia", Seminars in Hematology, vol. 34, No. 4, 1997, pp. 343-354.

Elsbach, P. et al., "Role of the bactericidal/permeability-increasing protein in host defence", Current Opinion in Immunlogy, vol. 10, No. 1, 1998, pp. 45-49.

Levy, O., "A neutrophil-derived anti-infective molecule: bactericidal/permeability-increasing protein", Antimicrobial Agents and Chemotherapy, vol. 44, No. 11, 2000, pp. 2925-2931.

Levy, O., "Antimicrobial proteins and peptides of blood: templates for novel antimicrobial agents", Blood, vol. 96, No. 8, 2000, pp. 2664-2672.

Beamer, L.J. et al., "Crystal structure of human BPI and two bound phospholipids at 2.4 angstrom resolution", Science, vol. 276, 1997, pp. 1861-1864.

Lockhart, D.J. et al., "Expression monitoring by hybridization to high-density oligonucleotide arrays", Nature Biotechnology, vol. 14, No. 13, 1996, pp. 1675-1680.

Serhan, C.N. et al., "Novel functional sets of lipid-derived mediators with anti-inflammatory actions generated from omega-3 fatty acids via cyclooxygenase 2-nonsteroidal anti-inflammatory durgs and transcellular processing", J. Exp. Med., vol. 192, No. 8, 2000, pp. 1197-1204.

Serhan, C.N. et al., "Resolvins: a family of bioactive products of mega-3 fatty acid transformation circuits initiated by aspirin treatment that counter proinflammation signals", J. Exp. Med., vol. 196, No. 8, 2002, pp. 1025-1037.

Canny, G. et al., "Lipid mediator-induced expression of bactericidal/permeability-increasing protein (BPI) in human mucosal epithelia", *Proc. Natl. Acad. Sci. USA,* vol. 99, No. 6, 2002, pp. 3902-3907.

Dharmsathaphom, K. et al., "Established intestinal cell lines as model systems for electrolyte transport studies", *Methods in Enzymology,* vol. 192, 1990, pp. 354-389.

Eckmann, L. et al., "Epithelial cells secrete the chemokine interleukin-8 in response to bacterial entry", *Infection and Immunity,* vol. 61, No. 11, 1193, pp. 4569-4574.

Higuchi, R. et al., "Kinetic PCR analysis: real-time monitoring of DNA amplification reactions", *Biotechnology,* vol. 11, 1993, pp. 1026-1030.

Taylor, C.T. et al., "Critical role of cAMP response element binding protein expression in hypoxia-elicited induction of epithelial tumor necrosis factor-a", *J. Biolog. Chem.,* vol. 274, No. 27, 1999, pp. 19447-19454.

Pfaffl, M.W., "A new mathematical model for relative quantification in real-time RT-PCR", *Nucletic Acids Research,* vol. 29, No. 9, 2001, pp. 2002-2007.

McCormick, B.A. et al., "*Salmonella typhimurium* attachment to human intestinal epithelial monolayers: transcellular signaling to subepithelial neurophils", *J. Cell Biology,* vol. 123, No. 4, 1993, pp. 895-907.

Colgan, S.P. et al., "Defective invitro motility of polymorphonuclear leukocytes of homozygotte and heterozygote Chediak-Higashi cats", *Vet. Immunol. Immunopathology,* 1992, pp. 205-227.

Weersink, A., et al., "Human granulocytes express a 550-kDa lipopolysaccharide-binding protein on the cell surface that is identical to the bactericidal/permeability-incresing protein", *J. Immunology,* vol. 150, No. 1, 1993, pp. 253-263.

Weiss, J. et al., "Purification and characterization of a potent bactericidal and membrane active protein from the granules of human polymorphonuclear leukocytes", *J. Biol. Chem.,* vol. 253, No. 8, 1978, pp. 2664-2672.

Kato, T. et al, "Production of Hydroxy Unsaturated Fatty Acids Using Crude Lipoxygenase Obtained from Infected Rice Plants", *Bull. Chem. Soc, Jpn.,* vol. 69, 1996, pp. 1663-1666.

De Montarby, L. et al., "Syntheses stereoselectives de metabolites hydroxyls d'acides gras polyinsatures", *Bulletin De La Societe Chimique de France,* No. 3, 1989, pp. 419-432.

Yamane, M. et al., "Docosahexanenoidarachidonic acid ω-hydroxylation system and differentiation in the human colonic adenocarcinoma cell line, Caco-2", *Cancer Letters,* vol. 122, 1998, pp. 51-59.

Iigo, M. et al, "Inhibitory effects of docosahexaenoic acid on colon carcinoma 26 metastasis to the lung", *Br. J. Cancer,* 1997, pp. 650-655.

Billman, G.E. et al., "Prevention of sudden cardiac death by dietary pure ω-3 polyunsaturated fatty acids in dogs", *Circulation* 99 1999, pp. 2452-2457.

Simopoulos, A.P., "Workshop on the essentiality of an recommended dietary intakes for omega-6 and omega-3 fatty acids", *J. Am. Coll. Nutr.* 1999, pp. 487-489.

Marchioloi, R., "Dietary supplementation with n-3 polyunsaturated fatty acids and vitamin E after myocardial infarction: results of the GISSI-Prevenzione trial", *Lancet* 1999, pp. 447-455.

Weissmann, G., "Aspirin", *Sci. Am.* 1991, pp. 84-90.

Marcus, A.J., "Platelets: their role in hemostasis, thrombosis, and inflammation", *Inflammation: Basic Principles and Clinical Correlates* 1999, pp. 77-95.

Claria, J. et al., "Aspirin triggers previously undescribed bioactive eicosanoids by human endothelial cell-leukocyte interactions", *Proc. Natl. Acad. Sci. USA* 1995, pp. 9475-9479.

Serhan, C.N. et al, "Design of lipoxin A4 stable analogs that block transmigration and adhesion of human neutrophils", *Biochemistry* 1995, pp. 14609-14615.

Chiang, N. et al., "Leukotriene B4 receptor transgenic mice reveal novel protective roles for lipoxins and aspirin-triggered lipoxins in reperfusion", *J. Clin. Invest.* 1999, pp. 309-316.

Herschman, H.R., "Recent progress in the cellular and molecular biology of prostaglandin synthesis", *Trends Cardiovasc. Med.* 1998, pp. 145-150.

Needleman, P. et al., "The discovery and function of COX-2", *J. Rheumatol* 1997, pp. 6-8.

Chiang, N. et al., "Aspirin-triggered 15-epi-lipoxin A4 (ATL) generation by human leukocytes and murine peritonitis exudates: Development of a specific 15-epi-LXA4 ELISA", *J. Pharmacol. Exp. Ther.* 1998, pp. 779-790.

Xiao, G. et al., "Analysis of hydroperoxide-induced tyrosyl radicals and lipoxygenase activity in aspirin-treated human prostaglandin H synthase-2", *Biochemistry* 1997, pp. 1836-1845.

Node, K. et al., "Anti-inflammatory properties of cytochrome P450 epoxygenase-derived eicosanoids", *Science* 1999, pp. 1276-1279.

Sethi, S. et al., "Inhibition of phagocyte-endothelium interactions by oxidized fatty acids: A natural anti-flammatory mechanism?", *J. Lab. Clin. Med.* 1996, pp. 27-38.

Levy, G.N., "Prostaglandin H synthases, nonsteriodal anti-inflammatory drugs, and colon cancer", *FASEB J.* 1997, pp. 234-247.

Gronert, K. et al., "Transcellular regulation of eicosanoid biosynthesis", *Eicosanoid Protocols* 1999, pp. 119-144.

George, H.J. et al., "Expression purification and characterization of recombinant human inductible prostaglandin G/H synthase from baculovirus-infected insect cells", *Protein Expres. Purif.* 1996, pp. 19-26.

Capdevila, J.H. et al., "The highly stereoselective oxidation of polyunsaturated fatty acids by cytochrome P450BM-3", *J. Biol. Chem.* 1996, pp. 22663-22671.

Ruettinger, R.T. et al., "Epoxidation of unsaturated fatty acids by a soluble cytochrome P-45-dependent system from *Bacillus megaterium*", *J. Biol. Chem.* 1981, pp. 5728-5734.

Lee, T.H. et al., "Characterization and biologic properties of 5,12-dihydroxy derivatives of eicosapentaenoic acid, including leukotriene B5 and the double lipoxygenase product", *J. BioL Chem.* 1984, pp. 2383-2389.

Serhan, C.N. et al., "Nomenclature of lipoxins and related compounds dervived from arachidonic acid and eicosapentaenoic acid", *Prostaglandins* 1987, pp. 201-204.

Hill, D.J. et al., "Trout thrombocytes contain 12-but not 5-lipoxygenase activity", *Biochim. Biophys. Acta* 1999, pp. 63-70.

Cronstein, B.N. et al., "A mechanism for the anti-inflammatory effects of corticosteriods: The glucocorticoid receptor regulates leukocyte adhesion to endotheliasl cells and expression of endothelial-leukocyte adhesion molecule 1 and intercellular adhesion molecule 1", *Proc. Natl. Acad. Sci.* 1992, pp. 9991-9995.

Yokomizo, T. et al., "A G-protein-coupled receptor for leukotriene B4 that mediates chemotaxis", *Nature* 1997, pp. 620-624.

Buchanan, M.R. et al., "Regulation of endothelial cell and platelet receptor-ligand binding by the 12- and 15-lipoxygenase monohydroxides, 12-, 15-HETE and 13-HODE", *Prostaglandins Leukot. Essent. Fatty Acids* 1998, pp. 339-346.

Ridker, P.M. et al., "Inflammation, aspirin, and the risk of cardiovascular disease in apparently healthy men", *N. Engl. J. Med.* 1997, pp. 973-979.

Stahl, G.L. et al., Pharmacologic profile of lipoxins A5 and B5: new biologically active eicosanoids European Journal of Pharmacology, 1989, vol. 163, No. 1, 99. 55-60.

Lloyd-Evans, P. et al., Eicosanoid generation and effects on the aggregation of thrombocytes from the rainbow trout, *Oncorhynchus mykiss*, Biochimica et Biophysica Acta, Lipids and Lipid Metabolism, 1994, vol. 1215, No. 3. pp. 291-299.

Yamane, M. et al., High-performance liquid chromatography-thermospray mass spectrometry of epoxy polyunsaturated fatty acids and epoxyhydroxy polyunsaturated fatty acids from an incubation mixture of rat tissue homogenate, Journal of Chromatography, B: Biomedical Sciences and Applications, 1994, vol. 652, No. 2, pp. 123-136.

Inhibitory potencies of fish oil hydroxyl fatty acids on cellular lipoxygenases and platelet aggregation, Biochemical Pharmacology, 1991, vol. 42, No. 4, p. 959-962.

\* cited by examiner

OKF-6

Caco2

2° only

APPROACH TO ANTIMICROBIAL HOST DEFENSE WITH MOLECULAR SHIELDS WITH EPA AND DHA ANALOGS

CROSS-REFERENCE TO RELATED APPLICATION(S)

This application is a continuation of U.S. patent application Ser. No. 10/323,867, filed Dec. 18, 2002, which claims benefit of U.S. Provisional Patent Application No. 60/342,138, filed on Dec. 18, 2001, both of which are incorporated by reference in its entirety.

STATEMENT REGARDING FEDERALLY SPONSORED RESEARCH

The work leading to this invention was supported in part by National Health Institutes of Health (NH) grants RO-1 DK50189 and PO-1 DE13499. The U.S. Government therefore may have certain rights in this invention.

BACKGROUND

During both acute and chronic inflammatory processes, epithelial cells coordinate mucosal responses to infection. For this reason, much recent attention has been paid to understanding innate, anti-inflammatory pathways utilized by mucosal epithelial cells. Of particular interest are small molecules that exhibit anti-inflammatory activity.

The initial encounter of microbes with human tissues and cells occurs at the level of mucosal tissues. Epithelial cells line all mucosal organs, and thus, the epithelium is the key interface for microbial interactions. Importantly, microorganisms which interact with mucosal surfaces may be beneficial (e.g. normal flora) or pathogenic (e.g. infectious agents), and as a result, epithelial cells have adapted mechanisms to selectively kill or inactivate invading microorganisms. As part of this arsenal, epithelial cells express antimicrobial peptides whose primary function includes killing of invading microorganisms. This family of unrelated peptides includes peroxidase, lactoferrin, lysozyme, phospholipase A2, secretory leukoprotease inhibitor (SLPI), and defensins (1). Among the innate anti-inflammatory and/or anti-infective defense molecules of humans is the bactericidal/permeability-increasing protein (BPI), a 55-60 kDa protein found in neutrophil azurophilic granules, on the neutrophil cell surface, and to a lesser extent, in specific granules of eosinophils (2-4). BPI selectively exerts multiple anti-infective actions against gram-negative bacteria, including cytotoxicity through damage to bacterial inner/outer membranes, neutralization of bacterial lipopolysaccharide (endotoxin), as well as serving as an opsonin for phagocytosis of gram-negative bacteria by neutrophils (3, 5). Structural characterization of BPI reveals a symmetrical bipartite molecule containing a cationic N-terminal region for antibacterial and endotoxin neutralization and a C-terminal motif necessary for bacterial opsonization (6).

Therefore, a need exists for the stimulation, production, and/or release of BPI from body tissues to help combat, for example, bacterial invasion and/or infection.

SUMMARY

Epithelial cells which line mucosal surfaces are the first line of defense against bacterial invasion and infection. Recent studies have also indicated that epithelial cells contribute significantly to the orchestration of ongoing inflammatory processes. The present invention provides that antimicrobial peptides expressed by human epithelial cells, including BPI (an antibacterial and endotoxin-neutralizing molecule previously associated with neutrophils), can be stimulated and its production increased in the presence of the compounds of the invention, discussed vide infra. Moreover, epithelial cells express antimicrobial peptides whose primary function includes killing of invading microorganisms. This family of unrelated peptides includes peroxidase, lactoferrin, lysozyme, phospholipase A2, secretory leukoprotease inhibitor (SLPI), and defensins (1). The present invention is intended to include the use of compounds presented herein for interaction with the peroxidase, lactoferrin, lysozyme, phospholipase A2, secretory leukoprotease inhibitor (SLPI), and defensins (1) and including BPI.

Moreover, the present invention provides that epithelial antimicrobial peptides, such as BPI, are transcriptionally regulated transcriptionally regulated by analogs of endogenously occurring anti-inflammatory molecules. Initial studies to verify microarray analysis revealed that epithelial cells of wide origin (oral and intestinal mucosa) express BPI and each is similarly regulated by compounds of the present invention. Studies aimed at localization of BPI revealed that such expression occurs on the cell surface of cultured epithelial cell lines and dominantly localizes to epithelia in human mucosal tissue. Functional studies employing a BPI-neutralizing anti-serum revealed that surface BPI blocks endotoxin-mediated signaling in epithelia and kills *Salmonella typhimurium*. These studies identify a previously unappreciated "molecular shield" for protection of mucosal surfaces against Gram-negative bacteria and their endotoxin.

It has been surprisingly discovered that eicosapentaenoic acid (EPA) analogs and docosahexaenoic acid (DHA) analogs of the invention, discussed infra, can be utilized for the stimulation and increased secretion of bactericidal permeability increasing protein (BPI) from various tissues, i.e., mucosal cells, epithelial cells, for combating infection and/or the invasion of bacteria in a subject. Consequently, the compounds disclosed herein are useful for the treatment and prevention of infection by bacteria in a subject.

Recent findings indicate dietary omega-3 PUFA's can be converted into novel lipid mediators which function to promote the resolution of inflammation (8, 9). The present invention provides that bioactive eicosapentanoic acid (EPA, C20:5) derived products influence BPI expression.

Compositions of the present invention provide novel lipid mediators produced from EPA and/or DHA that significantly influence BPI expression. The present invention provides that fortification of the mucosal molecular shield (10) by the compositions of the present invention contributes to the resolution phase of active inflammatory disease.

According to one aspect of the invention, increased production or release of BPI protein by a subject's tissue(s), stimulated by one or more compounds of the invention, provide alleviation of many disease states or conditions associated with endotoxin mediated effects. For example, such endotoxin mediated effects include, but are not limited to: increases in circulating tumor necrosis factor (TNF), soluble TNF receptors p55 and p75 (sTNFr (p55) and sTNFr (p75)), interleukin 6 (IL-6), interleukin 8 (IL-8), interleukin 10 (IL-10) and increased neutrophil degranulation characterized by increased circulating lactoferrin and/or elastase/alpha 1 antitrypsin complexes (EAA); increases in circulating tissue plasminogen activator antigen (tPA Ag), tissue plasminogen activator activity (tPA act), and alpha 2-plasmin inhibitor-plasmin (PAP) complexes, plasminogen activator inhibitor antigen (PAI Ag) and urokinase type plasminogen activator (uPA); decrease in lymphocytes; increases in thrombin/antithrombin III (TAT) complexes; and decreases in systemic vascular resistance index (SVRI) and increases in cardiac index (CI).

BPI is a potent and specific bactericidal compound. The disease targets include, for example, sepsis and infectious diseases, and provide a non-antibiotic mechanism to fight infectious disease caused by Gram negative bacteria. Therefore, use of the therapeutic compounds of the invention to stimulate production of BPI by a subject, helps to treat, ameliorate, or prevent such disease.

According to another aspect of the invention, increased production or release of BPI protein by a subject's tissue(s), stimulated by one or more of the BPI inducing agents of the invention, provides for the use of a BPI protein inducing agent in the manufacture of a medicament for treatment of humans exposed to bacterial endotoxin. This aspect of the invention contemplates use of at least one BPI protein inducing agent in the manufacture of such medicaments in an therapeutically effective amount to alleviate endotoxin in tumor necrosis factor and interleukin 6; in an amount effective to alleviate endotoxin mediated increase in circulating interleukin 8 and in neutrophil degranulation as characterized by increased circulating lactoferrin and/or elastase/alpha 1 antitrypsin complexes; in an amount effective to alleviate endotoxin mediated changes in numbers of circulating lymphocytes; in an amount effective to alleviate endotoxin mediated increase in circulating tissue plasminogen activator and tissue plasminogen activator activity; in an amount effective to alleviate endotoxin-mediated decreases in systemic vascular resistance index; in an amount effective to treat sepsis; and in an amount effective to bacterial infections. This aspect of the invention further contemplates use of a BPI protein inducing agents in combination with bacterial antibiotics in the manufacture of such medicaments.

In another aspect, the present invention is directed to a packaged pharmaceutical composition for treating the activity or conditions described herein in a subject. The packaged pharmaceutical composition includes a container holding a therapeutically effective amount of at least one therapeutic compound of the invention, i.e., a BPI inducing agent, having one of the formulae described infra and instructions for using the therapeutic compound for treating the activity or condition in the subject.

BRIEF DESCRIPTION OF THE DRAWINGS

The invention will be more fully understood from the following detailed description taken in conjunction with the accompanying drawings, in which.

DETAILED DESCRIPTION

Figure 1:
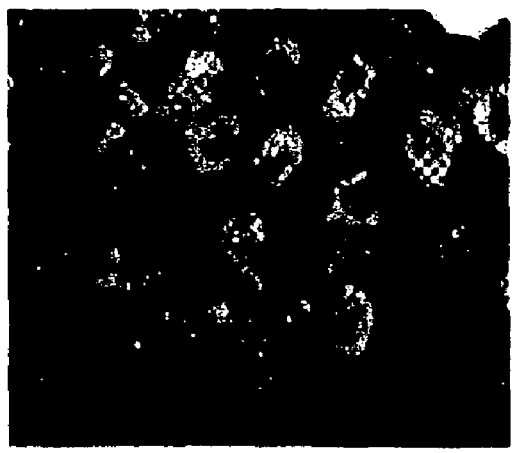
FIG. 1 depicts localization of BPI to the cell surface. BPI was localized by confocal microscopy in non-permeabilized OKF6 or Caco2 cells, as indicated. Shown in FIG. 2 are confocal sections through the mid-zone, sub-junctional portion of epithelial monolayers. Also shown is a control section omitting the primary Ab. Representative experiment from n=2.
Figure 1:
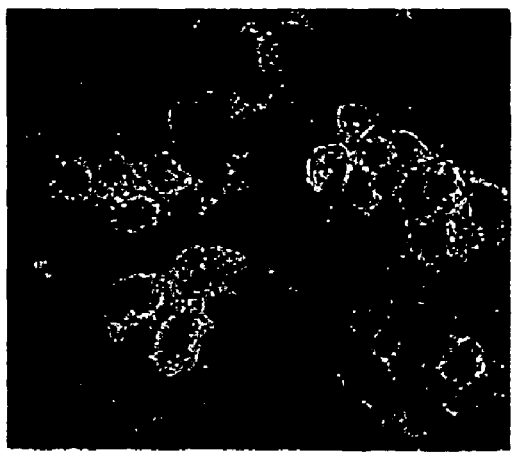
Figure 1:

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

Abbreviations used throughout the present application include the following and are included here for convenience. ATLM, aspirin-triggered lipid mediators; COX, cyclooxygenase I, II (isoforms); EC, endothelial cells; LC/MS/MS, liquid chromatography tandem mass spectrometry; LO, lipoxygenase; LT, leukotriene; PG, prostaglandins; PMN, polymorphonuclear leukocyte; EPA eicosapentaenoic acid; HEPE, hydroxyeicosapentaenoic acid; C20:5 (eicosapentanoic acid, EPA, an ω-3 fatty acid); and C22:6 (docosahexaenoic acid, DHA, an ω-3 fatty acid).

It has been surprisingly discovered that eicosapentaenoic acid (EPA) analogs and docosahexaenoic acid (DHA) analogs of the invention, discussed infra, can be utilized for the stimulation, release and increased secretion of bactericidal permeability increasing protein (BPI) from various tissues, i.e., mucosal cells, epithelial cells, for combating infection and/or the invasion of bacteria in a subject. Consequently, the compounds disclosed herein are useful for the treatment and prevention of infection in a subject.

According to one aspect of the invention, increased production or release of BPI protein by a subject's tissue(s), stimulated by one or more compounds of the invention, provide alleviation of many disease states or conditions associated with endotoxin mediated effects. For example, such endotoxin mediated effects include, but are not limited to: increases in circulating tumor necrosis factor (TNF), soluble TNF receptors p55 and p75 (sTNFr (p55) and sTNFr (p75)), interleukin 6 (IL-6), interleukin 8 (IL-8), interleukin 10 (IL-10) and increased neutrophil degranulation characterized by increased circulating lactoferrin and/or elastase/alpha 1 antitrypsin complexes (EAA); increases in circulating tissue plasminogen activator antigen (tPA Ag), tissue plasminogen activator activity (tPA act), and alpha 2-plasmin inhibitor-plasmin (PAP) complexes, plasminogen activator inhibitor antigen (PAI Ag) and urokinase type plasminogen activator (uPA); decrease in lymphocytes; increases in thrombin/antithrombin III (TAT) complexes; and decreases in systemic vascular resistance index (SVRI) and increases in cardiac index (CI).

BPI is a potent and specific bactericidal compound. The disease targets include, for example, sepsis and infectious diseases. The present invention provide a non-antibiotic mechanism to fight infectious disease caused by Gram negative bacteria. Therefore, use of the therapeutic compounds of the invention to stimulate production of BPI by a subject, helps to treat, ameliorate, or prevent such disease.

According to another aspect of the invention, increased production or release of BPI protein by a subject's tissue(s), stimulated by one or more of the compounds of the invention, provides for the use of a BPI protein inducing agent, i.e., the compounds of the invention, for the manufacture of a medicament for treatment of humans exposed to bacterial endotoxin. This aspect of the invention contemplates use of at least one BPI protein inducing agent in the manufacture of such medicaments in an amount effective to alleviate endotoxin in tumor necrosis factor and interleukin 6; in an amount effective to alleviate endotoxin mediated increase in circulating interleukin 8 and in neutrophil degranulation as characterized by increased circulating lactoferrin and/or elastase/alpha 1 antitrypsin complexes; in an amount effective to alleviate endotoxin mediated changes in numbers of circulating lymphocytes; in an amount effective to alleviate endotoxin mediated increase in circulating tissue plasminogen activator and tissue plasminogen activator activity; and in an amount effective to alleviate endotoxin-mediated decreases in systemic vascular resistance index. This aspect of the invention further contemplates use of a BPI protein inducing agents in combination with bacterial antibiotics in the manufacture of such medicaments.

The phrase "BPI inducing agent" is intended to include those compounds which cause BPI to be released from tissue(s), which cause the production of BPI to be increased relative to the normal stasis of the subject's physiology or stimulates production of BPI, or combinations thereof. In general, these compounds include EPAs and EPA analogs and DHAs and DHA analogs. These inducing agents cause BPI to become more readily available within the subject to combat disease or infection which results from the disease process. Therefore, the compounds of the invention indirectly act upon the disease process by stimulating the increased production and/or release of BPI which in turn prophylactically or therapeutically treats the disease. As described above, the disease process may be associated with bacteria. Therefore, the compounds are useful for the treatment of these conditions such that the physiological effects associated with the disease state or condition are inhibited, decreased, or eradicated.

Aspirin Triggered Lipid Mediators (EPA and DHA Analogs)

A class of compounds useful for the disease states and conditions (maladies) described herein include those referred to as "aspirin triggered lipid mediators" and are derived from eicosapentanoic acid, (EPA), an ω-3 fatty acid (C20:5) or docosahexaenoic acid, (DHA), also an ω-3 fatty acid (C22:6).

In one aspect of the invention, an EPA analog useful as a BPI inducing agent in the treatment of the disease states or conditions described throughout the specification has the formula:

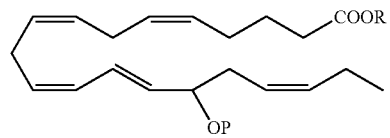

In a preferred embodiment, the hydroxyl at the carbon 15 position has an R configuration. In another embodiment, the hydroxyl at the carbon 15 position has an S configuration. Alternatively, the hydroxyl at the carbon 15 position is an R/S racemic mixture.

In another aspect of the invention, an EPA analog useful as a BPI inducing agent in the treatment of the disease states or conditions described throughout the specification has the formula:

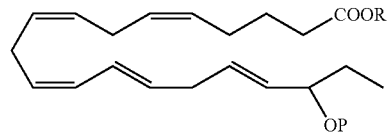

In a preferred embodiment, the hydroxyl at the carbon 18 position has an R configuration. In another embodiment, the hydroxyl at the carbon 18 position has an S configuration. Alternatively, the hydroxyl at the carbon 18 position is an R/S racemic mixture.

In still another aspect of the invention, an EPA analog useful as a BPI inducing agent in the treatment of the disease states or conditions described throughout the specification has the formula:

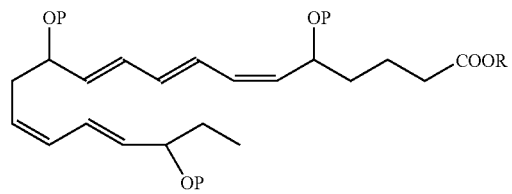

In one embodiment, the hydroxyl at the carbon 5 position has an S configuration, the hydroxyl at the carbon 6 position has an R configuration and the hydroxyl at the carbon 15 position has an R configuration. In another embodiment, the hydroxyl at the carbon 5 position has an R/S configuration, the hydroxyl at the carbon 6 position has an R/S configuration and the hydroxyl at the carbon 15 position has an R/S configuration.

In yet another aspect of the invention, an EPA analog useful as a BPI inducing agent in the treatment of the disease states or conditions described throughout the specification has the formula:

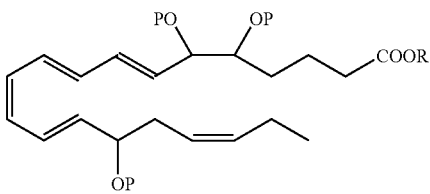

In one embodiment, the 5-hydroxyl has an S configuration, the 12-hydroxyl has an R configuration and the 18-hydroxyl has an R configuration. In another embodiment, the 5-hydroxyl has an R/S configuration, the 12-hydroxyl has an R/S configuration and the 18-hydroxyl has an R/S configuration.

In one aspect of the invention, a DHA analog useful as a BPI inducing agent in the treatment of the disease states or conditions described throughout the specification has the formula:

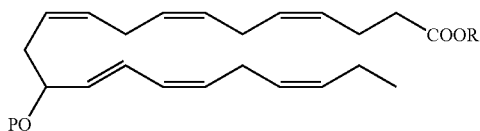

designated as 13-hydroxy-DHA, where P=H (hydroxyl). In one embodiment, the 13-hydroxyl has an S configuration. In another embodiment, the 13-hydroxyl has an R configuration. In still another embodiment, the 13-hydroxyl is a racemic mixture, e.g., an R/S configuration.

In another aspect of the invention, a DHA analog useful as a BPI inducing agent in the treatment of the disease states or conditions described throughout the specification has the formula

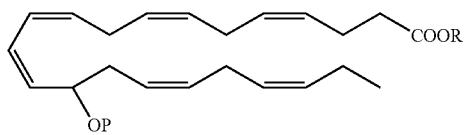

designated as 14-hydroxy-DHA, where P=H (hydroxyl). In one embodiment, the 14-hydroxyl has an S configuration. In another embodiment, the 14-hydroxyl has an R configuration. In still another embodiment, the 14-hydroxyl is a racemic mixture, e.g., an R/S configuration.

In still another aspect of the invention, a DHA analog useful as a BPI inducing agent in the treatment of the disease states or conditions described throughout the specification has the formula

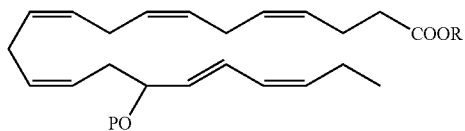

designated as 16-hydroxy-DHA, where P=H. In one embodiment, the 16-hydroxyl has an S configuration. In another embodiment, the 16-hydroxyl has an R configuration. In still another embodiment, the 16-hydroxyl is a racemic mixture, e.g., an R/S configuration.

In yet another aspect of the invention, a DHA analog useful as a BPI inducing agent in the treatment of the disease states or conditions described throughout the specification has the formula

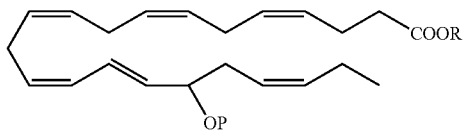

designated as 17-hydroxy-DHA, where P=H. In one embodiment, the 17-hydroxyl has an S configuration. In another embodiment, the 17-hydroxyl has an R configuration. In still another embodiment, the 17-hydroxyl is a racemic mixture, e.g., an R/S configuration.

In yet another aspect of the invention, a DHA analog useful as a BPI inducing agent in the treatment of the disease states or conditions described throughout the specification has the formula

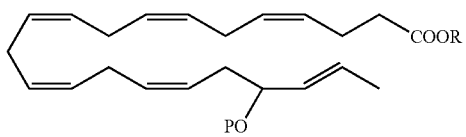

designated as 19-hydroxy-DHA, where P=H. In one embodiment, the 19-hydroxyl has an S configuration. In another embodiment, the 19-hydroxyl has an R configuration. In still another embodiment, the 19-hydroxyl is a racemic mixture, e.g., an R/S configuration.

In another aspect of the invention, a DHA analog useful as a BPI inducing agent in the treatment of the disease states or conditions described throughout the specification has the formula

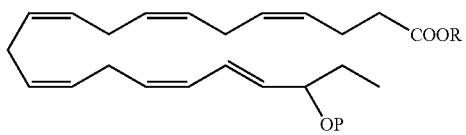

designated as 20-hydroxy-DHA, where P=H. In one embodiment, the 20-hydroxyl has an S configuration. In another embodiment, the 20-hydroxyl has an R configuration. In still another embodiment, the 20-hydroxyl is a racemic mixture, e.g., an R/S configuration.

In the EPA and DHA compounds, R is a hydrogen atom or is a pharmaceutically acceptable salt, ester, e.g., methyl ester, amide or prodrug. Preferred analogues include methyl, ethyl and glycerol esters.

In the EPA and DHA analogs, it should be understood that reference to "hydroxyl" stereochemistry is exemplary, and that the term is meant to include protected hydroxyl groups as well as the free hydroxyl group.

The hydroxyl(s) in the EPA and DHA analogs can be protected by various protecting groups (P), such as those known in the art. An artisan skilled in the art can readily determine which protecting group(s) may be useful for the protection of the hydroxyl group(s). Standard methods are known in the art and are more fully described in literature. For example, suitable protecting groups can be selected by the skilled artisan and are described in Green and Wuts, "Protecting Groups in Organic Synthesis", John Wiley and Sons, Chapters 5 and 7, 1991, the teachings of which are incorporated herein by reference. Preferred protecting groups include methyl and ethyl ethers, TMS or TIPPS groups, acetate or proprionate groups and glycol ethers, such as ethylene glycol and propylene glycol derivatives.

For example, one or more hydroxyl groups can be treated with a mild base, such as triethylamine in the presence of an acid chloride or silyl chloride to facilitate a reaction between the hydroxyl ion and the halide. Alternatively, an alkyl halide can be reacted with the hydroxyl ion (generated by a base such as lithium diisopropyl amide) to facilitate ether formation.

It should also be understood that for the EPA and DHA analogs, not all hydroxyl groups need be protected. One, two or all three hydroxyl groups can be protected. This can be accomplished by the stoichiometric choice of reagents used to protect the hydroxyl groups. Methods known in the art can be used to separate the mono, di- or tri-protected hydroxy compounds, e.g., HPLC, LC, flash chromatography, gel permeation chromatography, crystallization, distillation, etc.

It should be understood that there are one or more chiral centers in each of the above-identified compounds. It should understood that the present invention encompasses all stereochemical forms, e.g., enantiomers, diastereomers and racemates of each compound.

The EPA and DHA analogs described herein are the subject of pending U.S. Ser. No. 09/785,866, the contents of which are hereby incorporated in their entirety. U.S. Ser. No. 09/785,866 further provides methods of preparation and isolation of the EPA and DHA analogs.

The term "recognition site" or receptor is art-recognized and is intended to refer generally to a functional macromolecule or complex of macromolecules with which certain groups of cellular messengers, such as hormones, leukotrienes, EPA analogs, or DHA analogs must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a DHA or EPA analog upon which an enzyme or an enzyme and its cofactor attempts to perform one or more metabolic transformations which that enzyme or enzyme and cofactor normally transform on DHA or EPA analogs. The metabolic transformation region may or may not be susceptible to the transformation.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled analog" is further understood to encompass compounds which are labeled with radioactive isotopes, such as but not limited to tritium ($^3$H), deuterium ($^2$H), carbon ($^{14}$C), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes an EPA or DHA analog. The blockage or reduction may occur by covalent bonding, by irreversible binding, by reversible binding which has a practical effect of irreversible binding, or by any other means which prevents the enzyme from operating in its usual manner on another EPA or DHA analog.

The term "resists metabolism" is meant to include failing to undergo one or more of the metabolic degradative transformations by at least one of the enzymes which metabolize EPA analogs or DHA analogs.

The term "more slowly undergoes metabolism" means having slower reaction kinetics, or requiring more time for the completion of the series of metabolic transformations by one or more of the enzymes which metabolize EPA analogs or DHA analogs.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo.

The term "subject" is intended to include living organisms susceptible to conditions or diseases caused or contributed bacteria and pathogens as generally disclosed, but not limited to, throughout this specification. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one BPI inducing agent, in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of a BPI inducing agent can be administered as ear drops to treat otitis.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the BPI inducing agent(s) of the invention. A "therapeutically effective amount" refers to an amount effective, at dosages and for periods of time necessary, to achieve the desired therapeutic result, e.g., a diminishment or prevention of effects associated with various disease states or conditions. A therapeutically effective amount of the BPI inducing agent may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the BPI inducing agent and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a BPI inducing agent of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Delivery of the BPI inducing agents of the present invention to the lung by way of inhalation is an important method of treating a variety of respiratory conditions (airway inflammation) noted throughout the specification, including such common local conditions as bronchial asthma and chronic obstructive pulmonary disease. The BPI inducing agents can be administered to the lung in the form of an aerosol of particles of respirable size (less than about 10 μm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations should be dispensed in a manner that produces particles or droplets of respirable size.

Once prepared an aerosol formulation is filled into an aerosol canister equipped with a metered dose valve. The formulation is dispensed via an actuator adapted to direct the dose from the valve to the subject.

Formulations of the invention can be prepared by combining (i) at least BPI inducing agent in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. Conventional neoprene and buna valve rubbers used in metered dose valves for delivering conventional CFC formulations can be used with formulations containing HFC-134a or HFC-227. Other suitable materials include nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Formulations of the invention can be contained in conventional aerosol canisters, coated or uncoated, anodized or unanodized, e.g., those of aluminum, glass, stainless steel, polyethylene terephthalate.

The formulation(s) of the invention can be delivered to the respiratory tract and/or lung by oral inhalation in order to effect bronchodilation or in order to treat a condition susceptible of treatment by inhalation, e.g., asthma, chronic obstructive pulmonary disease, etc. as described throughout the specification.

The formulations of the invention can also be delivered by nasal inhalation as known in the art in order to treat or prevent the respiratory conditions mentioned throughout the specification.

While it is possible for a compound of the present invention to be administered alone, it is preferable to administer the compound as a pharmaceutical composition.

The invention features an article of manufacture that contains packaging material and a BPI inducing formulation contained within the packaging material. This formulation contains an at least one BPI inducing agent and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable BPI inducing agents, include EPA analogs and DHA analogs described herein.

More specifically, the invention features an article of manufacture that contains packaging material and at least one BPI inducing agent contained within the packaging material. The packaging material contains a label or package insert indicating that the formulation can be administered to the subject to asthma in an amount, at a frequency, and for a duration effective treat or prevent symptoms associated with such disease states or conditions discussed throughout this specification.

Methods

EPA and DHA Analogue Identification and Preparation

Zymosin, hematin, NADPH, and ASA were from Sigma-Aldrich. EPA (Cayman Chemical) and other synthetic standards, hydroxy fatty acids, and intermediates used for identification were purchased from Cascade Biochem Ltd. *Bacillus megaterium* was from American Type Culture Collection. Materials used in liquid chromatography random mass spectrometry (LC/MS/MS) analyses were from vendors given in (Gronert, K., C. B. Clish, M. Romano, and C. N. Serhan. 1999. Transcellular regulation of eicosanoid biosynthesis. In Eicosanoid Protocols. E. A. Lianos, editor. Humana Press, Totowa, N.J. 119-144).

Human PMNs were freshly isolated from venous blood of healthy volunteers (that declined taking medication for 2 wk before donation; Brigham and Women's Hospital protocol no. 88-02642) by Ficoll gradient and enumerated. Human umbilical vein or microvascular ECs (HUVECs or HMVECs, respectively) were cultured for transendothelial migration (Serhan, C. N., J. F. Maddox, N. A. Petasis, I. Akritopoulou-Zanze, A. Papayianni, H. R. Brady, S. P. Colgan, and J. L. Madara. 1995. Design of lipoxin $A_4$ stable analogs that block transmigration and adhesion of human neutrophils. *Biochemistry* 34:14609-1461), HMVEC monolayers (one, two, or three passages) were seeded (~$2\times10^5$ cells/cm$^2$) on polycarbonate permeable supports precoated with 0.1% gelatin for incubations with NSAIDs and PUFA.

Inflammatory exudates were initiated with intrapouch injection of TNF-α (R&D Systems) into 6 d dorsal air pouches with (7) 6-8-wk-old male FVB mice (fed standard rodent diet 5001 containing 0.26% n-3 fatty acids) followed by ASA (500 µg) at 3.5 h and 300 µg C20:5/pouch at 4 h. At 6 h, pouches were lavaged (3 ml saline), and exudate cells were enumerated and activated 94 µM $A_{23187}$, 37° C., 20 min). Inhibition of TNF-α-stimulated (100 ng/pouch, FVB strain) PMN infiltration with intravenous tail injection of 18 R-hydroxyeicosapentaenoic acid (HEPE), 5, 12, 18R-HEPE analogue was determined (7) with pouch lavages taken at 4 h.

Specific [$^3$H]LTB$_4$, (NEN Life Science Products) binding was performed with human embryonic kidney (HEK) 293 cells stably transfected with human LTB$_4$ receptor (Chiang, N., K. Groner, C. B. Clish, J. A. O'Brien, M. W. Freeman, and C. N. Serhan. 1999, Leukotriene B$_4$ receptor transgenic mice reveal novel protective roles for lipoxins and aspirin-triggered lipoxins in reperfusion. *J Clin. Invest.* 104:309-316). Human recombinant COX-2 was overexpressed in 5/9 insect cells (American Type Culture Collection) with microsomal fractions (~8 µl) suspended in Tris (100 mM, pH 8.0) as in George, H. J., D. E. Van Dyk, R. A. Straney, J. M. Trzaskos, and R. A. Copeland. 1996. Expression purification and characterization of recombinant human inducible prostaglandin G/H synthase from baculovirus-infected insect cells. *Protein Expres. Purif.* 7:19-26. NSAIDs were incubated (i.e., ASA ~1 mM) at 37° C. for 30 min before addition of PUFA (20 µM), and conversions were also monitored using 1-$^{14}$C-labeled C20:5 (NEN Life Science Products).

For biogenic synthesis of intermediates and reference compounds, *B. megaterium* was grown in Bacto Nutrient Broth (Fisher Scientific) at 30° C. with shaking. To prepare standards for 18R-HEPE, a biogenic synthesis was used with *B. megaterium* sonicates incubated with NADPH (2 mM) and C20:5 (EPA) (330 µM) in 2 M Tris buffer. pH 8.1. Similar conditions were employed to convert LTB$_5$ (15 µM) to novel products. Incubations were extracted with deuterium-labeled internal standards for LC/MS/MS analysis using a Finnigan LCQ equipped with a LUNA C18-2 (150×2 mm; 5 µM) column and a rapid spectra scanning UV/Vis detector. Also, a Chiralcel CB-H column (J. T. Baker) was used to determine R and S alcohol configurations of monohydroxy-PUFA using isocratic (hexane/isopropanol 96:4 vol/vol). Detailed procedures for isolation, quantification, and structural determination of lipid-derived mediators were recently reported and used here essentially as described for the elucidation of the novel products.

Preparation of Hydroxy-DHA Compounds

Hydroxy-DHA compounds were prepared in vitro using recombinant COX-II, both in the presence and absence of aspirin acetylation. Briefly, an incubation mixture was prepared using recombinant human COX-II that was purified as a membrane preparation from SF9 cells expressing the enzyme. The enzyme was suspended in 400 µl of 1 M Tris buffer (pH 8.0) containing 5 mM phenol. For aspirin acetylation of COX-II, aspirin (2 mM) was added to the mixture and incubated at 37° C. for 30 minutes. DHA (5 µM) was then added and the incubated for 5 minutes at 37° C. The reaction was stopped with the addition of 400 µl of chilled methanol. The products were then extracted using solid phase extraction cartridges (SepPak C18).

The novel DHA compounds, 13-hydroxy-DHA, 14-hydroxy-DHA, 16-hydroxy-DHA, 17-hydroxy-DHA, 19-hydroxy-DHA or 20-hydroxy-DHA, have potencies equivalent to those described above for the compounds derived from EPA.

Epithelial Cell Culture

Caco2 intestinal epithelial cells were grown and maintained as confluent monolayers on collagen coated permeable supports as previously described in detail (11), and utilized 6-12 days after plating. The cervical epithelial line (Hela cells) were grown as described previously (12).

Transcriptional Analysis

The transcriptional profile of epithelial cells (Caco2 cells) exposed to indicated concentrations of 5S,12R,18R-tri-HEPE (18R-series EPA analogs) was assessed in RNA using real-time PCR (iCycler, BioRad, Hercules, Calif.), as described previously (13). Analysis of mRNA levels was performed using DNAse treated total RNA as previously described (14), using the following primer sets; human BPI sense (5'-GCA CCT GTT CCT GAT GGG-3' (SEQ ID NO:1)) and antisense primer (5'-AGC ACA AAT GGA AAT TTC TTG-3' (SEQ ID NO:2), 255 bp product); and human β-actin sense (5'-TGA CGG GGT CAC CCA CAC TGT GCC CAT CTA-3' (SEQ ID NO:3)) and antisense primer (5'-CTA GAA GCA TTT GCG GTG GAC GAT GGA GGG-3' (SEQ ID NO:4), 661 bp product))] in identical reactions was used to control for starting template. Transcript levels and fold-change in mRNA was determined as described previously (15).

Bacterial Killing Assays

*Salmonella typhimurium* (strain 14028 from American Type Culture Collection, Rockville, Md.) were cultured and grown in Luria broth as previously described (16). In subsets of experiments, *Enterococcus faecalis* (strain PCI 1326 from American Type Culture Collection, Rockville, Md.) were cultured as previously described (17). Caco2 epithelial cells were grown to confluence of 60 mm petri dishes and exposed to indicated experimental conditions. Cells were washed once with HBSS, and washed bacteria were added to epithelial monolayers at a ratio of 50 bacteria per adherent epithelial cell. Incubations were allowed to proceed for 90 minutes or as indicated on a rotating platform. Parallel samples omitting epithelial cells were used as controls. Following incubation, supernatants were collected and epithelial cells were hypotonically lysed with 1 ml ice cold water. Bacteria were pelleted, dilutions of both pellets and supernatants were plated, incubated overnight at 37° C., and colony counts were performed. In subsets of experiments, anti-BPI antisera (1:300 in HBSS) or anti-BPI antisera pre-adsorbed with rBPI (1:300 in HBSS), as indicated, were added 30 minutes prior to incubation with bacteria. Data are presented as the mean±S.E.M. CFU.

Localization of BPI in Human Tissue

Normal human esophageal or colonic specimens were obtained under an approved human institutional review board protocol. Sections were fixed in 10% buffered formalin, paraffin embedded, and sectioned using standard methods. Antigen retrieval was performed in a pressure cooker with EDTA Decloaker solution, pH 8.0 (Zymed Labs, San Francisco, Calif.) according to manufacturers recommendations. Sections were stained with rabbit polyclonal BPI antisera (1:100) and peroxidase-coupled secondary antibody (1 µg/ml, Zymed Labs, San Francisco, Calif.) and visualized by peroxidase method according to manufacturers recommendations (Vectastain, Vector Laboratories, Burlingame, Calif.). Control sections were incubated with BPI pre-adsorbed Ab (1:100 dilution), as indicated. Sections were visualized with a Nikon E600 microscope at 200× magnification.

Results

Epithelial Cells Express BPI and Such Expression is Regulated by EPA Analogs

Compositions of the present invention provide novel lipid mediators produced from EPA and/or DHA that significantly influence BPI expression. The present invention provides that fortification of the mucosal molecular shield (10) by the compositions of the present invention contributes to the resolution phase of active inflammatory disease.

Figure 5:
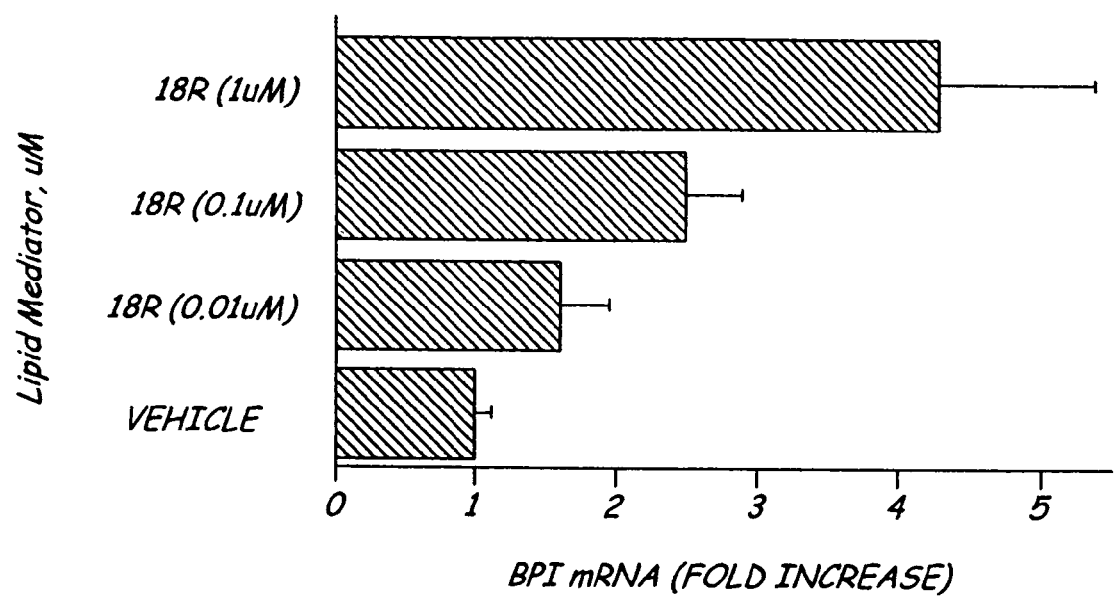
FIG. 5 depicts BPI induction by 18R-series EPA analogs. Confluent Caco2 intestinal epithelial monolayers were exposed to indicated concentrations of 5S,12R,18R-tri-HEPE (1 μM) for 24 hr. These results demonstrate quantitative real-time PCR for BPI in epithelial cells exposed to indicated conditions. β actin transcript was examined under similar conditions as an internal standard, and data represent the mean±S.E.M. fold induction of BPI mRNA by 5S,12R, 18R-tri-HEPE.

FIG. 5 depicts BPI induction by 18R-series EPA analogs. Confluent Caco2 intestinal epithelial monolayers were exposed to indicated concentrations of 5S,12R,18R-tri-HEPE (1 µM) for 24 hr. These results demonstrate quantitative real-time PCR for BPI in epithelial cells exposed to indicated conditions. β actin transcript was examined under similar conditions as an internal standard, and data represent the mean±S.E.M. fold induction of BPI mRNA by 5S,12R, 18R-tri-HEPE.

Localization of BPI Protein to the Epithelial Cell Surface

Previous studies have indicated that BPI can exist as a granule-bound protein or as a surface-associated protein on neutrophils (18). Initial attempts to detect soluble BPI using a sulfuric acid extraction known to release granule-bound BPI from neutrophils (19) (ELISA and western blot of soluble epithelial supernatants) revealed undetectable levels of BPI (sensitivity<100 pg/ml, data not shown). Thus, in an attempt to localize expression patterns of epithelial-expressed BPI, confocal microscopy was utilized on non-permeabilized epithelia. As shown in FIG. 1, BPI was expressed in a surface-bound form on both OKF-6 cells as well as Caco2 cells. The expression pattern was dominant on the lateral membrane surface, with some evidence for a punctate pattern in OKF6 cells.

Role of Surface BPI in Bacterial Killing

Figure 2:
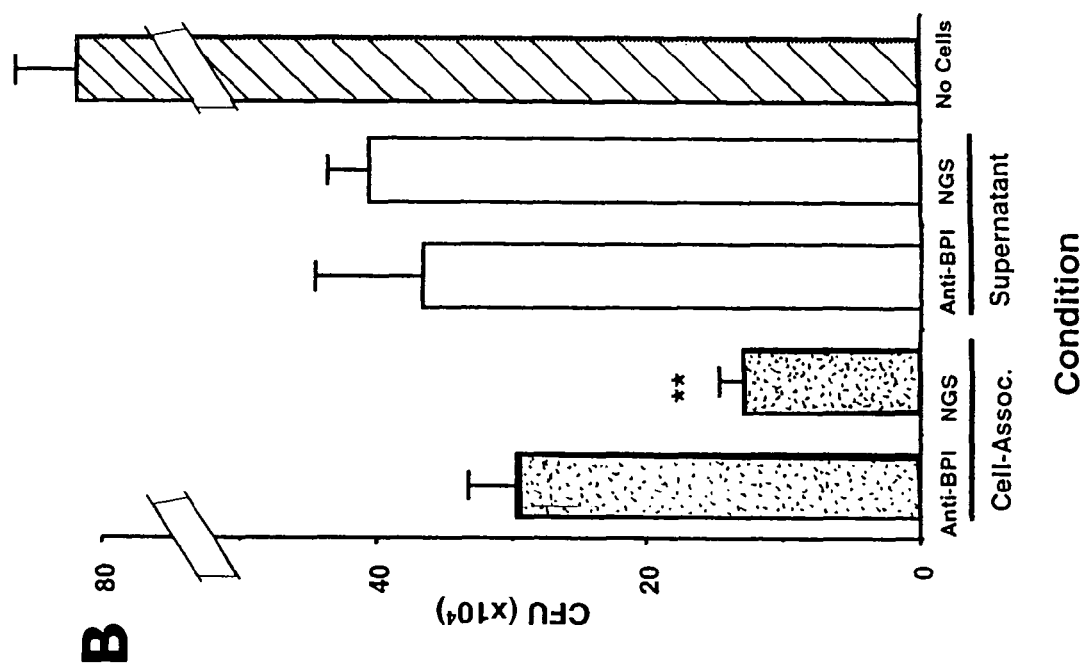
FIG. 2 depicts the role of epithelial BPI in bacterial killing. In panel A, adherent Caco2 cells were incubated with *S. typhimurium* at a ratio of 50 bacteria per epithelial cell and examined for killing over a 90 min period. Shown in FIG. 2 are pooled results from three experiments. In panel B, the role of BPI in Caco2 killing of *S. typhimurium* over a 60 min period was assessed by incubation of cells (Cell Assoc.) or supernatants with anti-BPI or NGS. The bacterial control omitting epithelial cells is also shown. Double asterix (**) indicates significantly different from anti-BPI, p<0.01).
Figure 2:
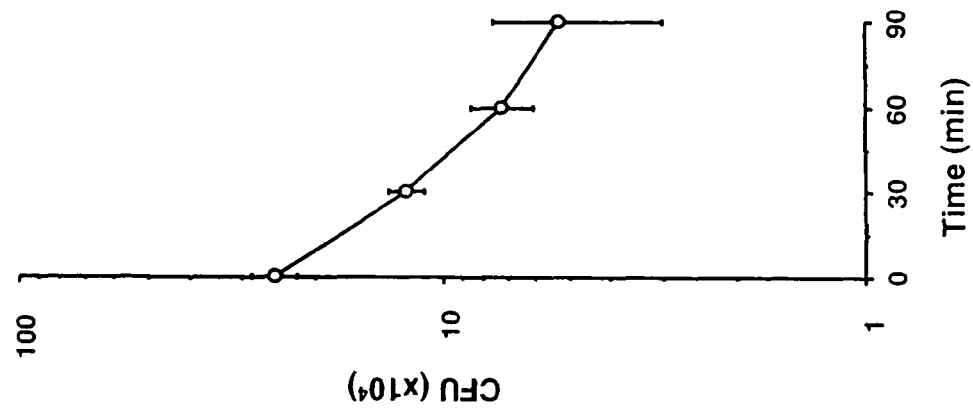
Figure 3:
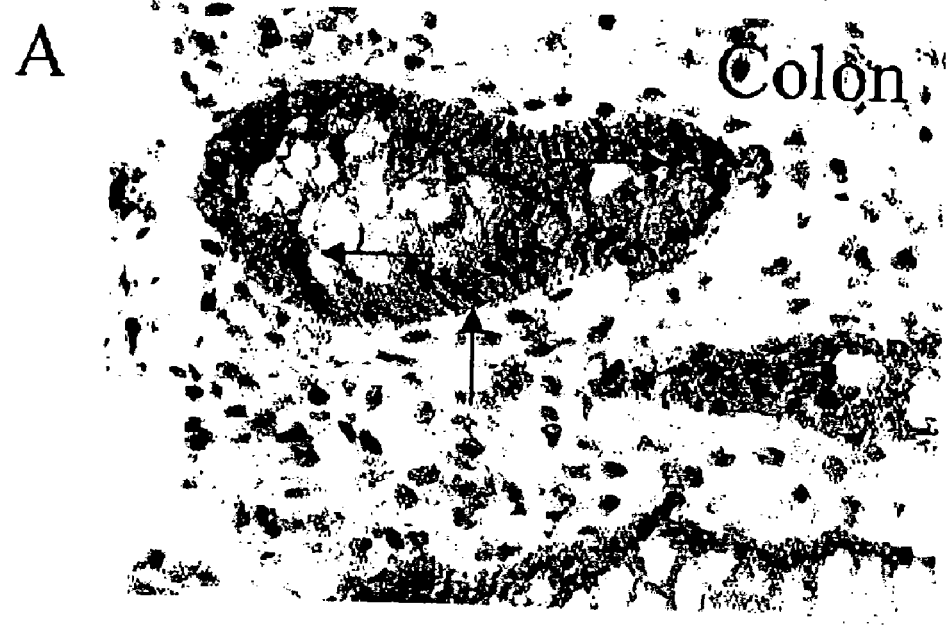
FIG. 3 depicts staining of normal human intestinal (panel A) and normal human esophagus (panel B) tissue for BPI. Arrows indicate predominant epithelial staining.
Figure 3:
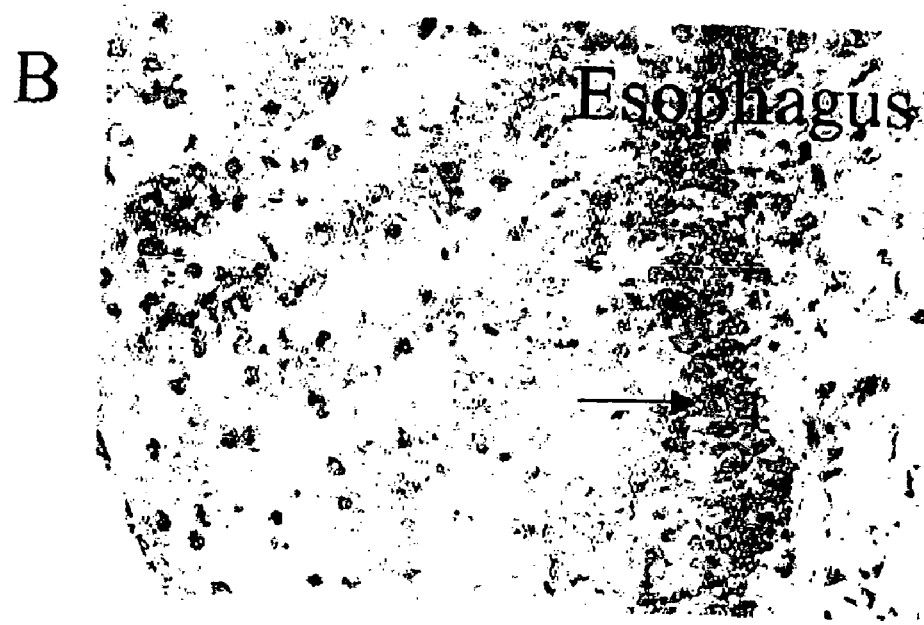

It was next determined whether intact, adherent epithelial cells kill a BPI-sensitive bacteria. Confluent Caco2 epithelial cells were exposed to *S. typhimurium* and examined for bacterial killing in standard colony-forming unit (CFU) analysis using adherent epithelial cells. As shown in FIG. 2A, such analysis revealed a nearly 1-log order reduction in CFU over a 90 min period (83±11% killing, p<0.025 by ANOVA). To define the role of BPI under such circumstances, similar studies were performed on adherent epithelial cells or soluble supernatants pre-exposed to anti-BPI or control NGS. As shown in FIG. 2B, anti-BPI exposure to adherent epithelia, but not soluble supernatants, significantly inhibited bacterial killing compared to control NGS (p<0.01). Parallel experiments assessing epithelial killing of a Gram-positive bacterium (*Enterococcus faecalis*) that is not sensitive to BPI indicated a smaller degree of killing (0.3±0.05-log order reduction in CFU over 90 min) but no influence of anti-BPI on such killing (5.5±2.1% decrease in killing, p=not significant).

Localization of BPI in Native Mucosal Tissue

Figure 4:
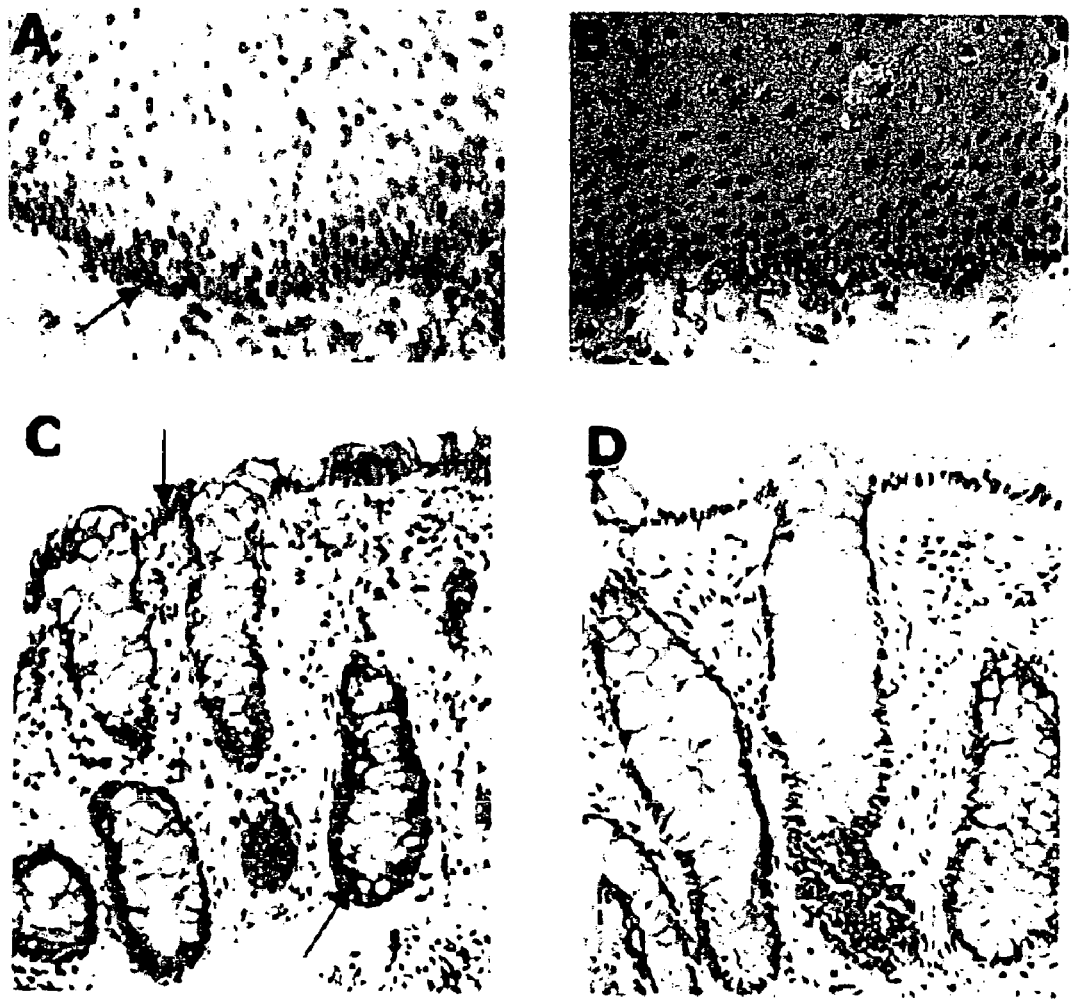
FIG. 4 depicts localization of epithelial BPI in human mucosal tissues. Normal human esophageal (panels A and B) or colon (panels C and D) specimens were obtained, fixed in 10% buffered formalin, paraffin embedded, and sectioned. Following antigen retrieval, sections were stained with rabbit polyclonal BPI antisera (panels A and C) or control sera (BPI pre-adsorbed Ab, panels B and D), followed by peroxidase-coupled secondary antibody, and then visualized by peroxidase method. Sections were visualized at 200× magnification. Arrows indicate areas of dominant BPI localization.

Further studies examined whether native tissues express BPI and whether such expression localizes to the epithelium. Since previous findings suggested that both columnar (e.g. T84 and Caco2 cells) and squamous epithelia (e.g. KB and OKF6 cells) express BPI, squamous and columnar epithelial bearing tissues (esophagus and colon, respectively) were examined. As shown in FIG. 4, analysis of normal human esophagus (panel A) and colon (panel C) sections revealed dominant localization of BPI to the epithelium. In the case of esophageal tissue, BPI was most strongly expressed at the transition zone between epithelia and the lamina propria, with graded decreasing expression toward surface epithelia. In the colon, BPI was expressed dominantly in crypt and villus epithelia, with less expression along the crypt-villus axis. In both the esophagus and colon, localization with pre-adsorbed anti-BPI revealed no specific signal (panels B and D, respectively). These findings in native human tissue demonstrate that BPI is expressed in vivo.

REFERENCES

1. Ganz, T., and J. Weiss. (1997) Antimicrobial peptides of phagocytes and epithelia. Semin Hematol 34, 343-54.
2. Elsbach, P., Weiss, J., (1998) *Curr Opin Immunol* 10, 45-9.
3. Ganz, T., Weiss, J., (1997) *Semin Hematol* 34, 343-54.
4. Levy, O., (2000) *Antimicrob Agents Chemother* 44, 2925-31.
5. Levy, O., (2000) *Blood* 96, 2664-72.
6. Beamer, L. J., Carroll, S. F., Eisenberg, D., (1997) *Science* 276, 1861-4.
7. Lockhart, D. J., Dong, H., Byrne, M. C., Follettie, M. T., Gallo, M. V., Chee, M. S., Mittmann, M., Wang, C., Kobayashi, M., Horton, H., Brown, E. L., (1996) *Nat Biotechnol* 14, 1675-80.
8. Serhan, C. N., Clish, C. B., Brannon, J., Colgan, S. P., Chiang, N., and Gronert, K. 2000. Novel functional sets of lipid-derived mediators with antiinflammatory actions generated from omega-3 fatty acids via cyclooxygenase 2-nonsteroidal antiinflammatory drugs and transcellular processing. *J Exp Med* 192:1197-1204.
9. Serhan, C. N., Hong, S., Gronert, K., Colgan, S. P., Devchand, P. R., Mirick, G., and Moussignac, R. L. 2002. Resolvins: a family of bioactive products of omega-3 fatty acid transformation circuits initiated by aspirin treatment that counter proinflammation signals. *J Exp Med* 196: 1025-1037.
10. Canny, G., Levy, O., Furuta, G. T., Narravula-Alipati, S., Sisson, R. B., Serhan, C. N., and Colgan, S. P. 2002. Lipid mediator-induced expression of bactericidal/permeability-increasing protein (BPI) in human mucosal epithelia. *Proc Natl Acad Sci USA* 99:3902-3907.
11. Dharmsathaphorn, K., and Madara, J. L. 1990. Established intestinal cell lines as model systems for electrolyte transport studies. *Methods Enzymol.* 192:354-389.
12. Eckmann, L., Kagnoff, M. F., and Fierer, J. 1993. Epithelial cells secrete the chemokine interleukin-8 in response to bacterial entry. *Infect Immun* 61:4569-4574.
13. Higuchi, R., Fockler, C., Dollinger, G., and Watson, R. 1993. Kinetic PCR analysis: real-time monitoring of DNA amplification reactions. *Biotechnology* 11:1026-1030.
14. Taylor, C. T., Fueki, N., Agah, A., Hershberg, R. M., and Colgan, S. P. 1999. Critical role of cAMP response element binding protein expression in hypoxia-elicited induction of epithelial TNFa. *J Biol. Chem.* 274:19447-19450.
15. Pfaffl, M. W. 2001. A new mathematical model for relative quantification in real-time RT-PCR. *Nucleic Acids Res* 29:E45-E45.
16. McCormick, B. A., Colgan, S. P., Delp-Archer, C., Miller, S. I., Madara, J. L., (1993) *J Cell Biol.* 123, 895-907.
17. Colgan, S. P., Blancquaert, M. A., Thrall, M. A., Bruyninckx, M. A., (1992) *Vet. Immunol. Immunopathol.* 31, 205-227.
18. Weersink, A. J., van Kessel, K. P., van den Tol, M. E., van Strijp, J. A., Torensma, R., Verhoef, J., Elsbach, P., Weiss, J., (1993) *J Immunol* 150, 253-63.
19. Weiss, J., Elsbach, P., Olsson, I., Odeberg, H., (1978) *J Biol Chem* 253, 2664-72.

One having ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A method for the stimulation of bactericidal permeability increasing protein (BPI) in a subject, comprising administering to a subject infected with BPI sensitive bacteria a therapeutically effective amount of a pharmaceutical composition comprising an eicosapentaenoic acid (EPA) analog or docosahexaenoic acid (DHA) analog and a pharmaceutically acceptable carrier, such that cells in the subject express increased levels of BPI, wherein the EPA analog is:

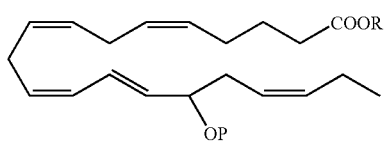

-continued

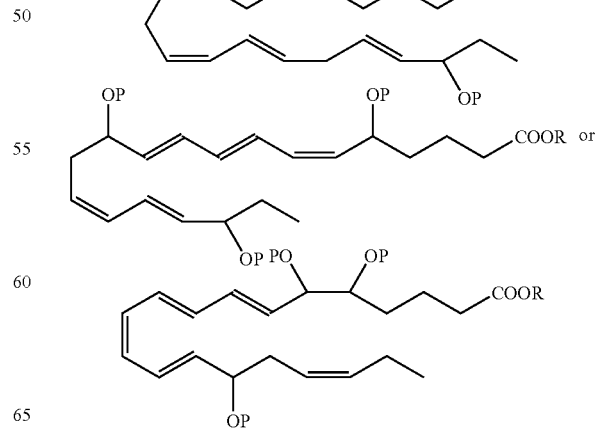

or
    wherein the DHA analog is:

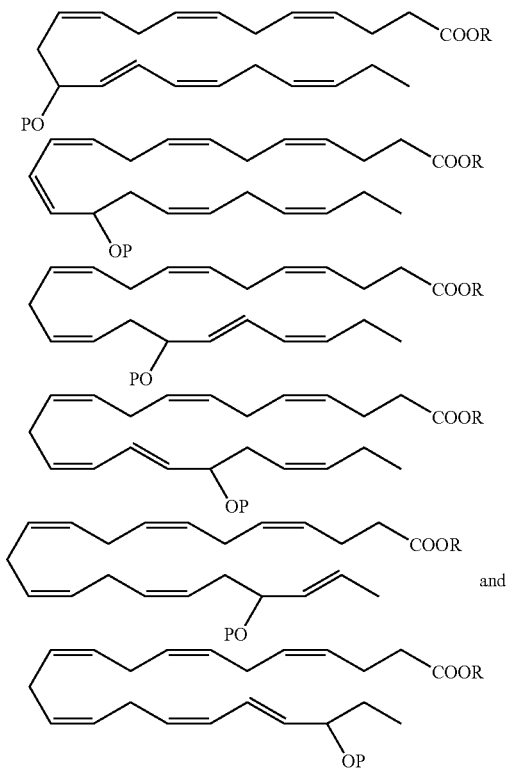

wherein each P is a hydrogen atom and R is a hydrogen atom or an alkyl group, or a pharmaceutically acceptable salt thereof.

2. A method for treating a bacterial infection in a subject, comprising administering to a subject infected with BPI sensitive bacteria a therapeutically effective amount of a pharmaceutical composition comprising an eicosapentaenoic acid (EPA) analog or docosahexaenoic acid (DHA) analog and a pharmaceutical carrier, such that cells in the subject express increased levels of BPI, thereby treating the BPI sensitive bacterial infection, wherein the EPA analog is:

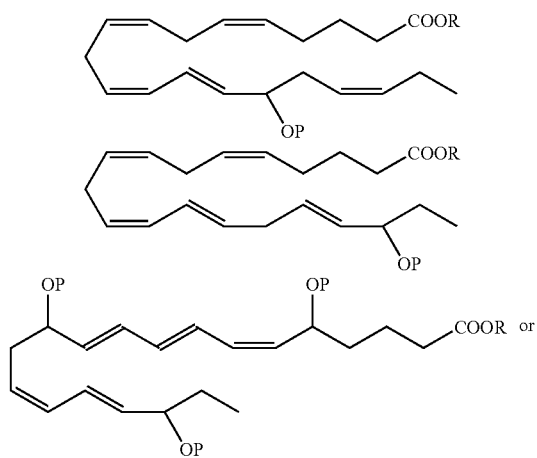

-continued

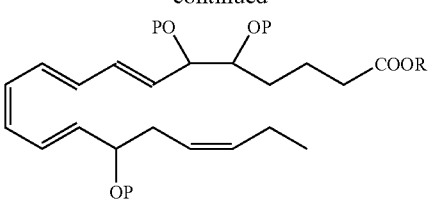

or
    wherein the DHA analog is:

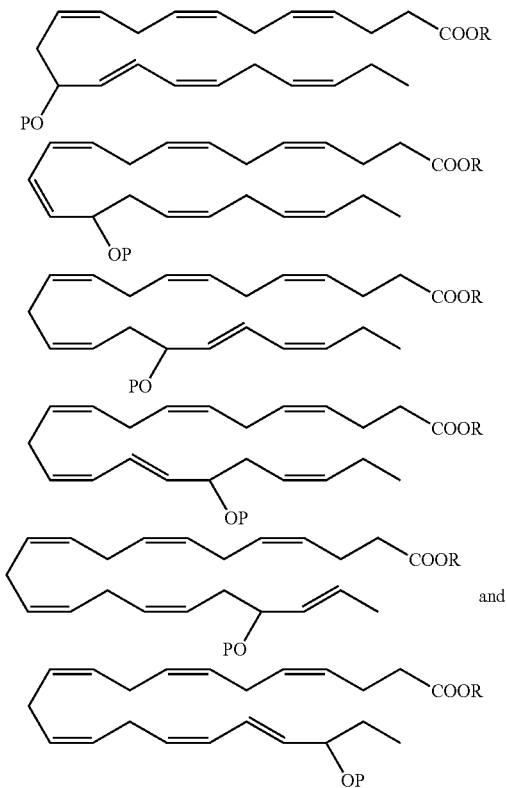

wherein each P is a hydrogen atom and R is a hydrogen atom or an alkyl group, or a pharmaceutically acceptable salt thereof.

3. A method for treating invasion by bacteria in a subject, comprising administering to a subject infected with BPI sensitive bacteria a therapeutically effective amount of a pharmaceutical composition comprising an eicosapentaenoic acid (EPA) analog or docosahexaenoic acid (DHA) analog and a pharmaceutical carrier, such that cells in the subject express increased levels of BPI, thereby treating the BPI sensitive bacterial invasion in the subject, wherein the EPA analog is:

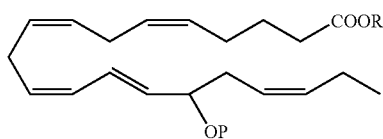

-continued

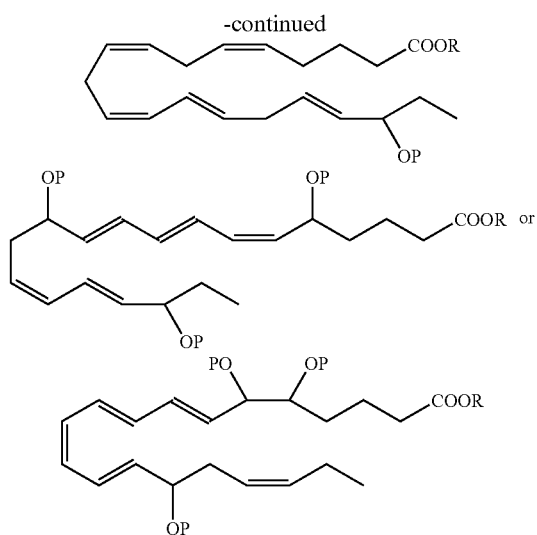

or
wherein the DHA analog is:

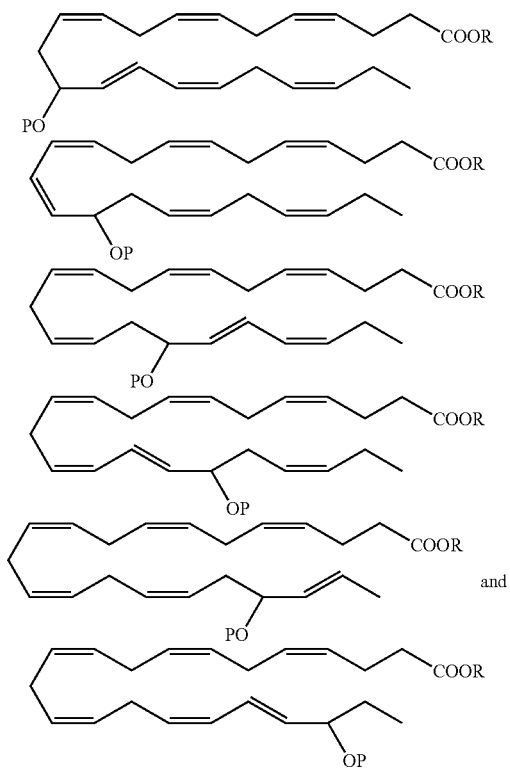

wherein each P is hydrogen atom and R is a hydrogen atom or an alkyl group, or a pharmaceutically acceptable salt thereof.

4. A method for the stimulation of bactericidal permeability increasing protein (BPI) in a subject, comprising administering to a subject infected with BPI sensitive bacteria a therapeutically effective amount of an eicosapentaenoic acid (EPA) analog or docosahexaenoic acid (DHA) analog, such that the cells in the subject express increased levels of BPI, wherein the EPA analog is:

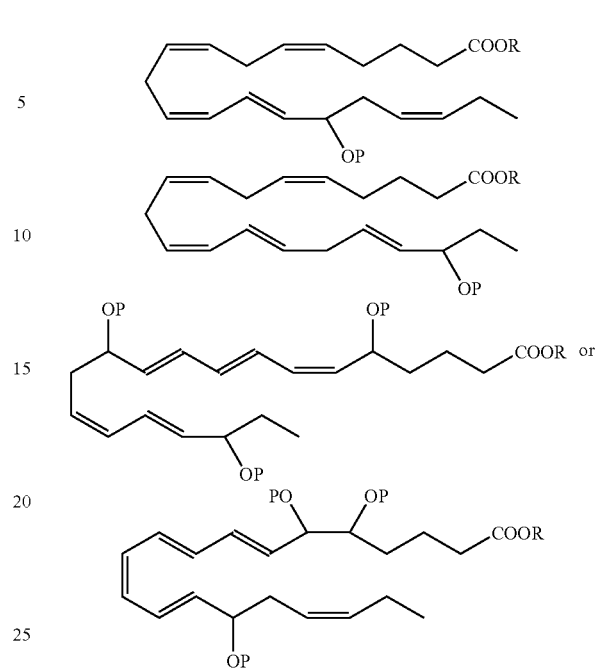

or
wherein the DHA analog is:

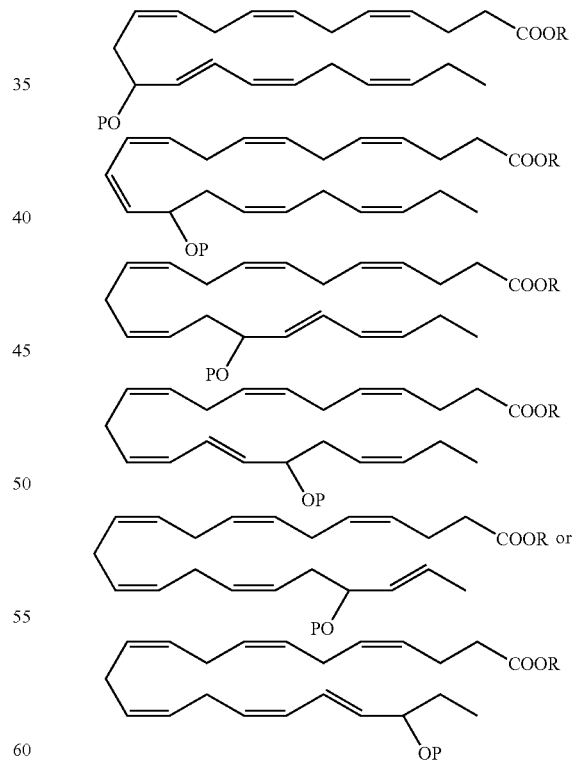

wherein each P is a hydrogen atom; and
R is a hydrogen atom or an alkyl group, or a pharmaceutically acceptable salt thereof.

5. A method for treating a bacterial infection in a subject, comprising administering to a subject infected with BPI sensitive bacteria a therapeutically effective amount of an eicosapentaenoic acid (EPA) analog or docosahexaenoic acid (DHA) analog, such that cells in the subject express increased levels of BPI, thereby treating the infection by the BPI sensitive bacteria, wherein the EPA analog is:

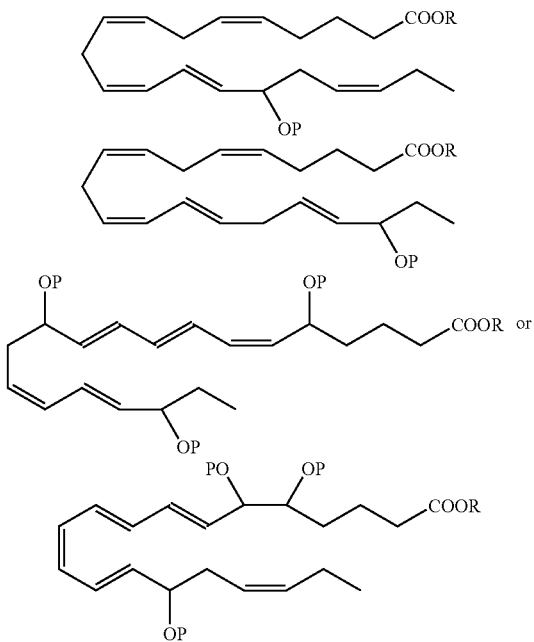

or
wherein the DHA analog is:

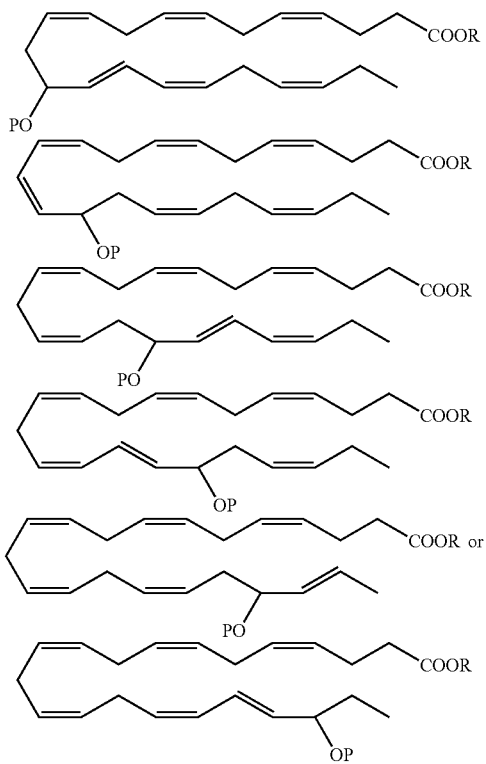

wherein each P is a hydrogen atom; and

R is a hydrogen atom or an alkyl group, or a pharmaceutically acceptable salt thereof.

6. A method for treating invasion by bacteria in a subject, comprising administering to a subject infected with BPI sensitive bacteria a therapeutically effective amount of an eicosapentaenoic acid (EPA) analog or a docosahexaenoic acid (DHA) analog, such that invasion by the BPI sensitive bacteria in a subject is treated, or such that mucosal cells in the subject express increased levels of BPI, thereby treating the invasion of the BPI sensitive bacteria, wherein the EPA analog is:

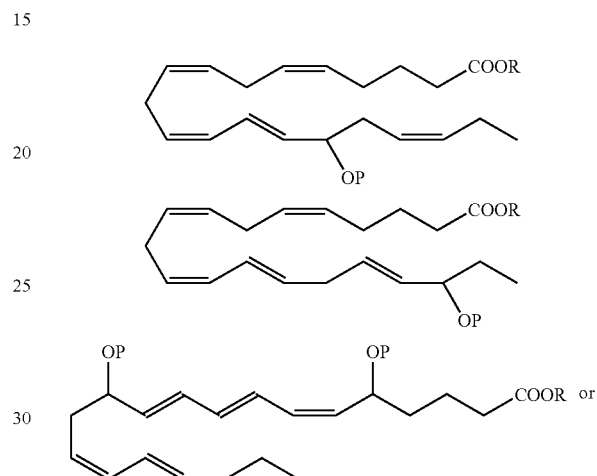

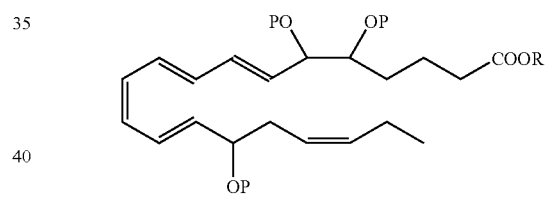

or
wherein the DHA analog is:

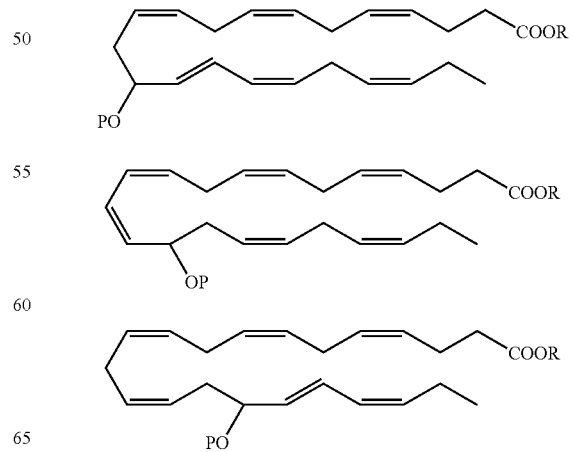

-continued
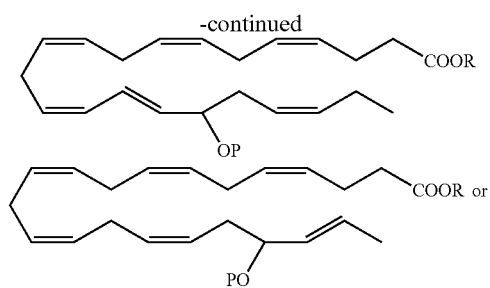
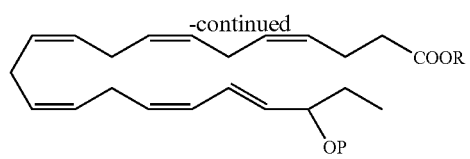
wherein each P is a hydrogen atom and R is a hydrogen atom or an alkyl group, or a pharmaceutically acceptable salt thereof.
* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial sequence
<220> FEATURE:
<223> OTHER INFORMATION: primer

<400> SEQUENCE: 1
gcacctgttc ctgatggg                                                 18

<210> SEQ ID NO 2
<211> LENGTH: 21
<212> TYPE: DNA
<213> ORGANISM: Artificial sequence
<220> FEATURE:
<223> OTHER INFORMATION: primer

<400> SEQUENCE: 2
agcacaaatg gaaatttctt g                                             21

<210> SEQ ID NO 3
<211> LENGTH: 30
<212> TYPE: DNA
<213> ORGANISM: Artificial sequence
<220> FEATURE:
<223> OTHER INFORMATION: primer

<400> SEQUENCE: 3
tgacggggtc acccacactg tgcccatcta                                    30

<210> SEQ ID NO 4
<211> LENGTH: 30
<212> TYPE: DNA
<213> ORGANISM: Artificial sequence
<220> FEATURE:
<223> OTHER INFORMATION: primer

<400> SEQUENCE: 4
ctagaagcat ttgcggtgga cgatggaggg                                    30